United States Patent [19]
Howland

[11] Patent Number: 5,330,473
[45] Date of Patent: Jul. 19, 1994

[54] BRANCH CONNECTOR FOR SPINAL FIXATION SYSTEMS

[75] Inventor: Robert S. Howland, Seal Beach, Calif.

[73] Assignee: Advanced Spine Fixation Systems, Inc., Cypress, Calif.

[21] Appl. No.: 26,518

[22] Filed: Mar. 4, 1993

[51] Int. Cl.$^5$ .............................................. A61B 17/56
[52] U.S. Cl. ........................................ 606/61; 403/396
[58] Field of Search ............... 606/61, 60, 62, 69, 606/73; 24/460, 461; 403/359, 396, 398, 399

[56] References Cited

U.S. PATENT DOCUMENTS

| | | | |
|---|---|---|---|
| 1,278,785 | 9/1918 | Tainter | 24/461 |
| 3,041,574 | 6/1962 | Cornell, Jr. | 403/396 |
| 3,997,138 | 12/1976 | Crock et al. | 248/67.5 |
| 4,653,481 | 3/1987 | Howland et al. | |
| 5,030,220 | 7/1991 | Howland | 606/61 |
| 5,084,049 | 1/1992 | Asher et al. | 606/61 |
| 5,152,701 | 10/1992 | Polidori | 403/399 |

FOREIGN PATENT DOCUMENTS 2612070  9/1988  France .

OTHER PUBLICATIONS

The Cross Medical Products, Inc. reference "PWB Transpedicular Spine Fixation System for Posterior Spine Fixation," p. 12.

Textbook of Spinal Surgery, edited by K. H. Bridwell and R. L. DeWald, vol. 1 (1991), Chapter 10, pp. 219-222.

Advanced Spine Fixation Systems, Inc. document, FIG. 4.

Primary Examiner—Tamara L. Graysay
Attorney, Agent, or Firm—Christie, Parker & Hale

[57] ABSTRACT

A branch connector is useful for connecting a pair of spine rods in a spinal fixation system. The branch connector includes an upper saddle, a lower saddle and a bolt for clamping the saddles together. The upper and lower saddles mate to define a pair of openings for receiving the spine rods. The bolt includes a threaded shaft that extends through a first aperture defined by the upper saddle and threads into a second aperture defined by the lower saddle. By tightening the bolt, the saddles are drawn together to securely grip the spine rods. The openings can be arranged in different configurations to perform different functions. A branch connector with parallel openings forms a branch clamp for connecting two spine rods in series. A pair of branch connectors arranged as transverse clamps with perpendicular openings can be combined with a transverse rod to form a cross brace assembly for bridging a pair of generally parallel spine rods.

28 Claims, 10 Drawing Sheets

BRANCH CONNECTOR FOR SPINAL FIXATION SYSTEMS

FIELD OF THE INVENTION

This invention relates to an implantable spinal fixation system for the surgical treatment of spinal disorders. More specifically, it relates to branch connectors for attaching the spine rods of spinal fixation systems to one another.

BACKGROUND OF THE INVENTION

Various types of spinal column disorders are known and include scoliosis (abnormal lateral curvature of the spine), kyphosis (abnormal backward curvature of the spine), lordosis (abnormal forward curvature of the spine), spondylolisthesis (forward displacement of a lumbar vertebra) and other disorders, such as ruptured or slipped discs, broken or fractured vertebrae and the like. Patients who suffer from such conditions usually experience extreme and debilitating pain. A technique known as spinal fixation uses surgical implants which mechanically immobilize areas of the spine causing the eventual fusion of the treated vertebrae. Such techniques have been used effectively to treat the above-described conditions and, in most cases, to bring to the patient relief from pain.

One particular technique for spinal fixation includes the immobilization of the spine by the use of a pair of spine rods that run generally parallel to the spine. In practicing this technique, bone screws are first fastened to the pedicles of the appropriate vertebrae or to the sacrum and act as the anchor points for the spine rods. The bone screws are generally placed two per vertebra, one at each pedicle on either side of the spinous process. Clamp assemblies join the spine rods to the screws. The spine rods are generally custom-bent to achieve the desired curvature of the spinal column. Examples of such spinal fixation devices can be found in U.S. Pat. Nos. 4,653,481 and 5,030,220, which are incorporated herein by reference. For some applications, rather than using bone screws, lamina hooks can be fastened to a spine rod to connect the rod to a vertebra for distraction or compression.

It has been found that when a pair of spine rods are fastened in parallel on either side of the spinous process, the assembly can be significantly strengthened by using at least one additional rod to horizontally bridge the pair of spine rods. One such cross brace assembly is known as the dynamic transverse traction assembly (DTT), and is used with fixation devices employing a pair of spine rods. A cross brace assembly very similar to the DTT is disclosed in U.S. Pat. No. 5,084,049. Devices such as these commonly consist of a threaded rod for providing the desired lateral support. The threaded rod is fastened to each of the spine rods by clamps located on each end of the threaded rod. These devices, while providing good lateral support, are generally bulky due to the fact that the transverse rod is placed above the plane containing the spine rods to be bridged. This bulkiness can lead to complications in that it can later cause irritation of the patient's back muscles and other tissue which might rub against the device. A cross brace assembly that fits closer to the spine, preferably in the same general plane as the vertical spine rods, would reduce the complications associated with bulkier devices.

In recognition of the complications associated with bulky spinal fixation devices, new systems generally known as "low profile" spinal fixation systems have been developed. A low profile branch connector is desirable for use with such low profile systems.

There is also a growing trend toward the use of spinal fixation devices in the upper regions of the spine, namely for fixation of the thoracic and cervical vertebrae. However, there are fundamental differences in the physiology and structure of the vertebrae in these regions of the spine compared to the lumbar and sacral regions. Because of these differences, the spinal fixation devices are generally designed differently from a device used in the lumbar and sacral regions. One primary difference is that a spinal fixation device for the cervical region of the spine must be smaller than one for the lumbar or sacral region. It is desirable that branch connectors such as branch clamps and transverse clamps be versatile enough that their size could be scaled down to accommodate these smaller spinal fixation systems.

It has also been found that when a spinal fixation device is to extend along several vertebrae, for example, a device fastened to the sacrum and extending up through the lumbar vertebrae, a significant amount of bending of the rod is required in order to properly seat it in the screw-clamps while still achieving the desired curvature of the spine. Such bending, while necessary, is generally undesirable not only because bending the rod to an intricate curve can be difficult, but also because sharp bends in the rod can cause a structural weakening of the rod. Furthermore, a spine rod that extends along a large portion of the spine can be difficult to securely fasten to each of several screw-clamps or lamina hooks.

It is desirable to ease the assembly of a spinal fixation device by using a pair of shorter segments of spine rods that can first be fastened to the appropriate portions of the spine and then joined together by a branch connector. Furthermore, a branch connector capable of connecting one size of spine rod to a different size spine rod is also desirable. Such a device would be useful in a long spinal fixation device that spans from, for example, the thoracic region of the spine through the cervical region. In such a device, different size rods could be used for the different regions of the spine, yet could still be fastened securely together.

While clamp assemblies for fastening a pair of spine rods to a single bone screw are known, such clamp assemblies are difficult to work with as the location of the clamp assembly is limited by the placement of the bone screw which must be located at a vertebra, preferably at a pedicle. A clamping assembly that connects a pair of spine rods independently of a bone screw is desirable.

Branch connectors are also useful in a spine fixation system that uses spine rods along with both screw-clamps and hooks. In a system that includes screw-clamps, rods are generally positioned more laterally from the centerline of the spine than the more medially positioned rods in a system that includes lamina hooks. A branch connector can be used to reduce the amount of rod bending that is required when switching from a lateral rod placement along one portion of the spine to a medial rod placement along another portion of the spine.

Any clamps used for joining spine rods should be designed for high strength, yet fast and simple installation. As the installation of a spinal fixation device entails a lengthy and complicated surgical procedure it should be recognized than any simplification of the assembly procedure of a spinal fixation device will tend to reduce the complications associated with the procedure.

SUMMARY OF THE INVENTION

A spinal fixation system has a clamp for connecting a first spine rod to a second rod. The clamp includes upper and lower saddles and clamping means. The upper and lower saddles mate to define a pair of openings. The first opening receives the first spine rod and the second opening receives the second rod. The clamping means generally comprises a bolt that extends through a first aperture defined by the upper saddle and threads into a second aperture defined by the lower saddle. By tightening the bolt, the saddles can be drawn together to securely grip the rods.

The configuration of the openings of a branch connector can be modified to perform various functions. In one embodiment, the openings are arranged generally parallel to one another to provide a branch clamp for connecting a pair of spine rods arranged in series across different vertebrae. In another embodiment the openings can be arranged generally perpendicular to one another to provide a transverse clamp that connects a transverse rod perpendicularly to a spine rod. A pair of such transverse clamps is used with a transverse rod to form a cross brace assembly between a generally parallel pair of spine rods.

BRIEF DESCRIPTION OF THE DRAWINGS

Features, aspects and advantages of the invention will be more fully understood when considered with respect to the following detailed description, appended claims and accompanying drawings where:

DETAILED DESCRIPTION

The present invention relates to branch connectors for use in connecting spine rods, the spine rods being part of a spinal fixation system useful for treating various spinal disorders. Such branch connectors can have various functions. A branch connector can be used as a branch clamp to connect a pair of spine rods that run in series in the same general direction along the spine, each rod being fastened to a different portion of the spine. A pair of modified branch connectors can also be used along with a transverse rod to form a cross brace assembly. Such a cross brace assembly is useful for providing additional lateral support to a pair of parallel spine rods fastened to the same general portions of the spine, but on opposite sides of the spinous process.

Figure 1:
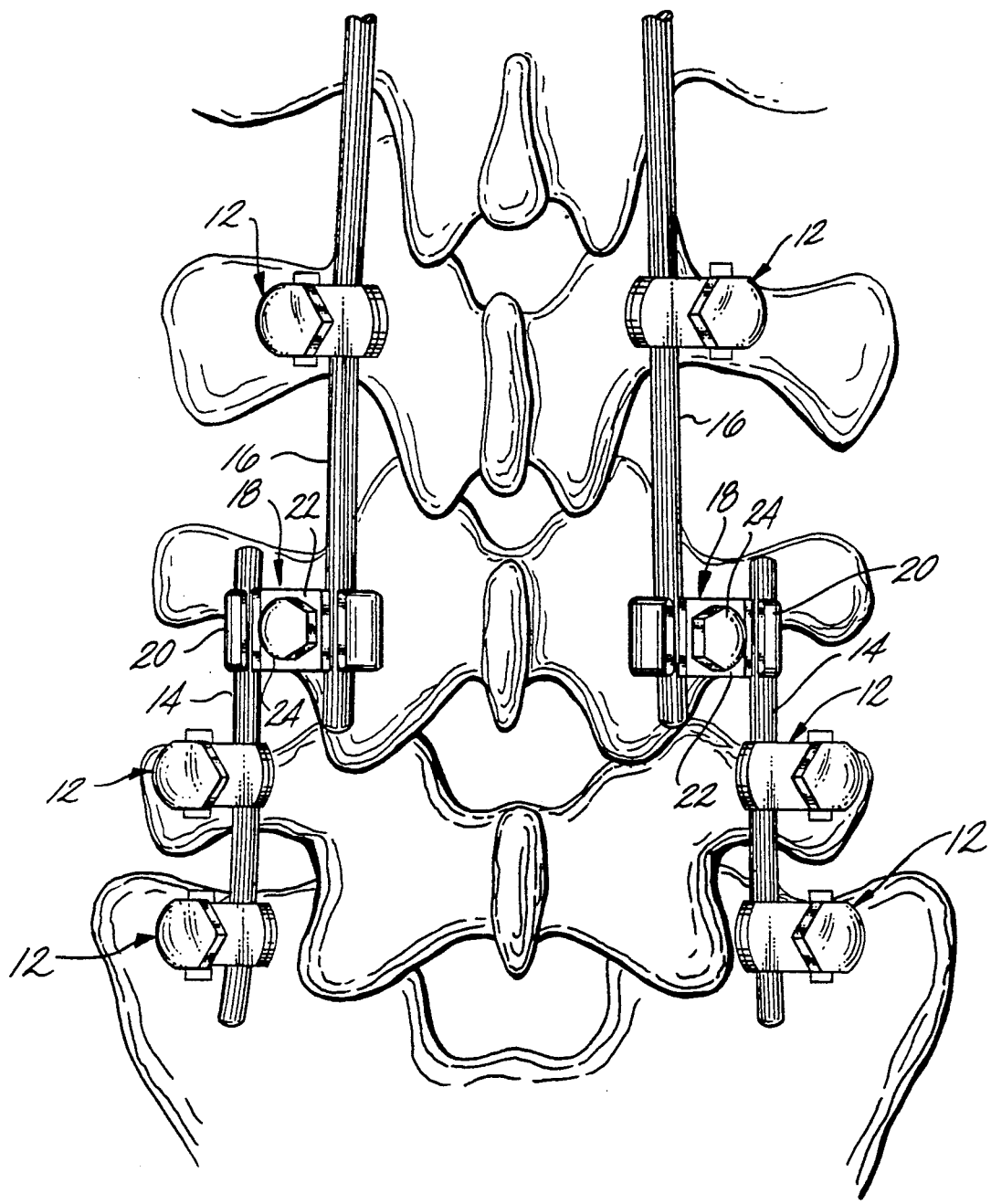
FIGS. 1 and 1a are diagrammatic posterior views of portions of two different spinal fixation systems, each of which includes a branch connector of the present invention installed on a portion of the spinal column.
Figure 1A:
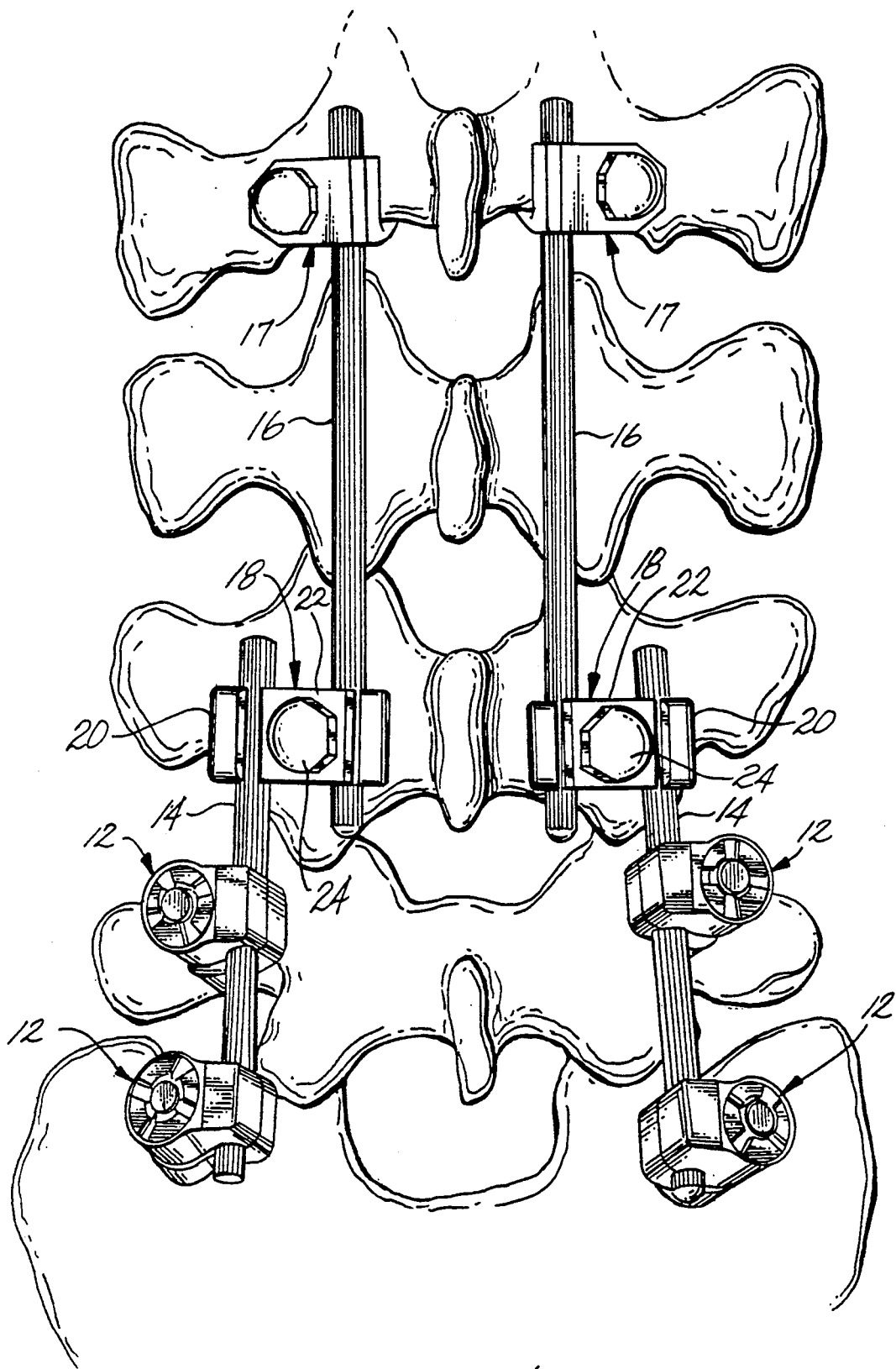

FIGS. 1, 1a, 2 and 3 illustrate various embodiments of branch connectors in place on a spine. These Figures illustrate spinal fixation systems that generally use rods, pedicle screws, lamina hooks and clamps to provide the necessary support for immobilizing a spine. Screw-and-clamp or "screw-clamp" assemblies 12 are fastened to the sacrum and in FIGS. 1, 1a and 2, to the pedicles of the fifth lumbar. The details of such general screw-clamp assemblies are known, for example, as described in U.S. Pat. Nos. 4,653,481 and 5,030,220. In FIGS. 1 and 1a, two pairs of spine rods provide the vertical support for each system. Spine rods 14 fasten to the screw-clamp assemblies 12 at the sacrum and the lower lumbar vertebra. In FIG. 1, spine rods 16 fasten to the screw clamp at the third lumbar vertebra and could extend further, possibly into the thoracic region of the spine (not shown). In FIG. 1a, spine rods 16 fasten to lamina hooks 17 at the second lumbar vertebra.

Segmented spine rods can be used for various reasons. They are particularly useful when the spine rods are to be attached over a large number of vertebrae. In such an application, a long spine rod can be very cumbersome and difficult to install. It is easier to attach a number of different segments of spine rods to various portions of the spine. Once fastened to their respective screw clamp assemblies, the rods can then be clamped to one another in series by branch connectors of this invention. Another reason for using segments of spine rod rather than one continuous spine rod is that in the lower lumbar and sacral region, the screw clamp assemblies are generally installed a greater distance laterally from the centerline of the spine as compared to the screw-clamp assemblies or lamina hooks located higher on the spine. As a result, a sharp bend in the spine rod would often be required to properly position the rod. To avoid such a sharp bend in the spine rod, it is easier to use segmented spine rods which are first fastened to the appropriate screw-clamps, and then fastened to one another with a branch connector of the present invention. Because the spine rods are received in slightly spaced apart openings of the branch connector, less bending of the rods is necessary. Of course, the ends of the spine rods that are to be joined must be appropriately bent a small amount so that the spine rods will properly seat in the openings.

A branch connector provides still other benefits in a spinal fixation system that uses both screw-clamps and lamina hooks. In using a lamina hook to connect a spine rod to a vertebra, the rod is ideally positioned in a medial location near the center line of the spine. On the other hand, the ideal rod placement for a system using screw-clamps is more lateral to the centerline of the spine. A branch clamp is a useful way to combine a lamina hook system to a screw-clamp system without the need for a sharp bend in the spine rod.

In all embodiments it is preferred that the branch connectors be placed independently of the bone screws. A branch connector that is fastened to a bone screw is difficult to work with as its location is determined by the placement of the bone screw. Keeping the branch connector independent of a bone screw allows much greater flexibility in its placement.

Figure 2:
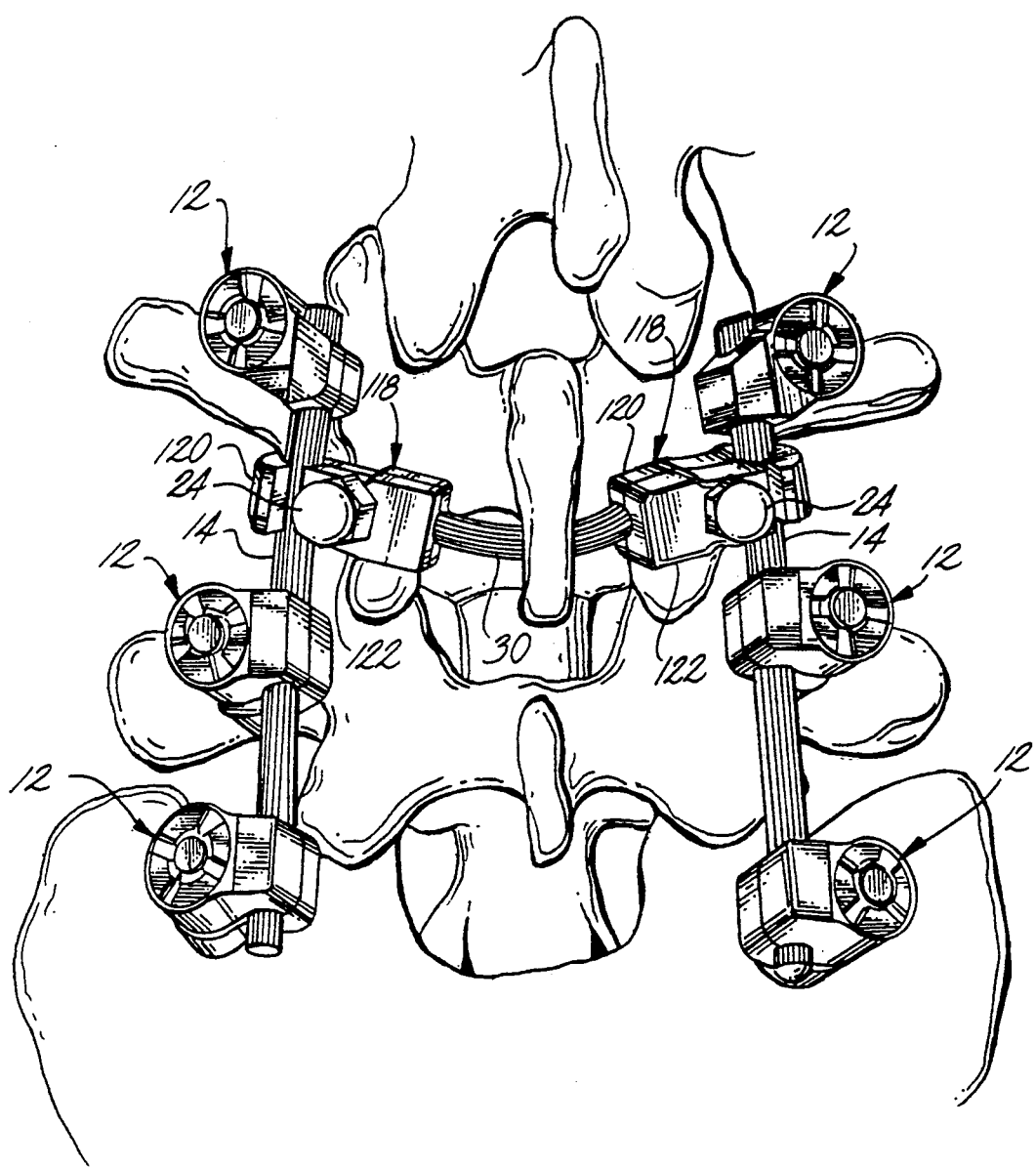
FIG. 2 is a diagrammatic posterior view of a spinal fixation system including a cross brace assembly of the present invention installed on a portion of the spinal column.
Figure 3:
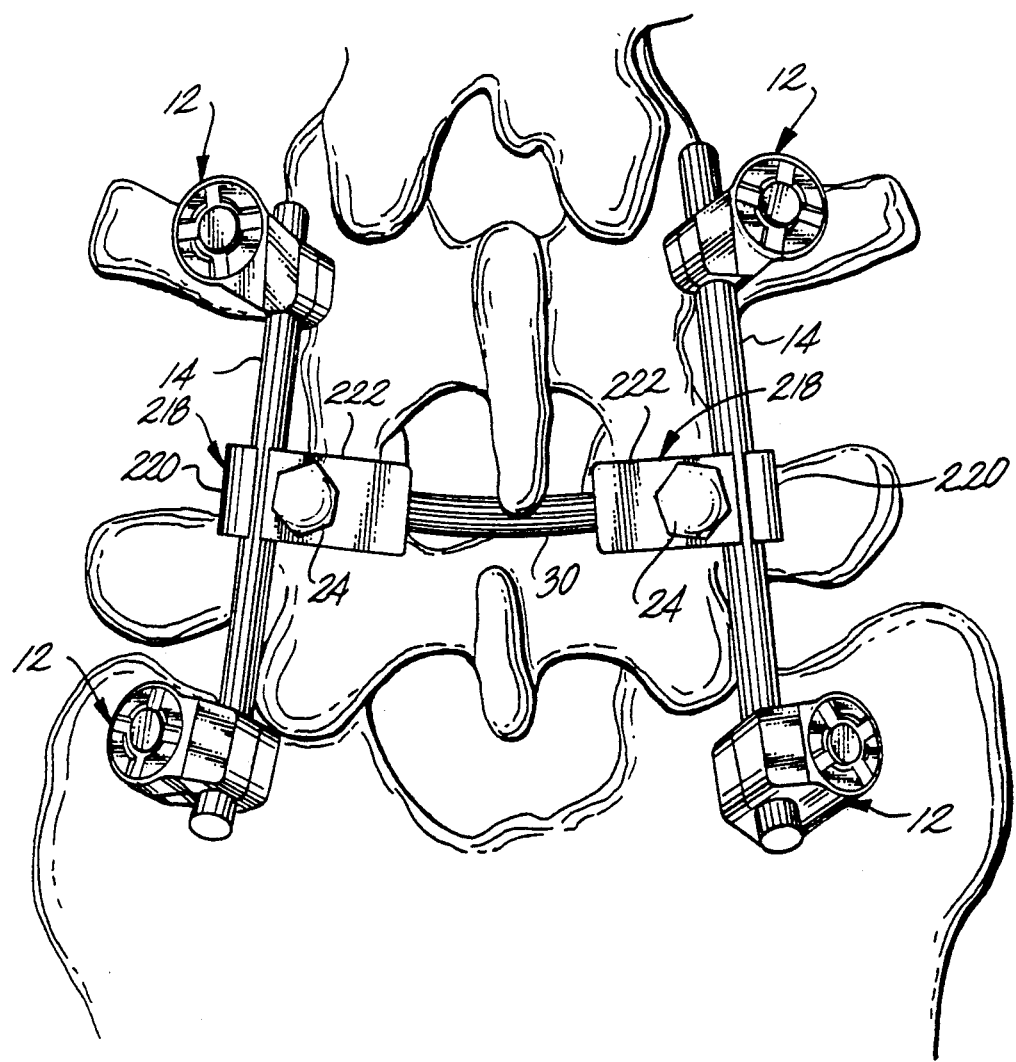
FIG. 3 is a diagrammatic posterior view of a spinal fixation system including an alternate embodiment of a cross brace assembly of the present invention installed on a portion of the spinal column.

In the embodiment of a branch connector of FIGS. 1 and 1a, each branch clamp 18 includes a lower saddle 20 and an upper saddle 22 which mate to define a pair of openings for receiving spine rods 14 and 16. Bolt 24 is used to clamp the saddles together to securely grip the rods. FIGS. 1-3 show rods that include longitudinally extending serrations as these rods can be gripped more securely by the various screw-clamps and branch connectors having mating teeth.

In FIGS. 2 and 3 variations of a branch connector used as a part of a cross brace assembly are shown. A pair of spine rods 14 are fastened to the pedicles and sacrum with screw-clamps 12. In FIG. 2, transverse clamps 118 and transverse rod 30 cooperate to form a cross brace assembly that bridges the spine rods. Such a cross brace assembly is useful in providing additional lateral support to the spinal fixation system. Each transverse clamp includes a lower saddle 120 which mates with upper saddle 122 to define a pair of openings. One opening receives spine rod 14 and the other opening receives an end of transverse rod 30. Bolt 24 is used to clamp the two saddles together to firmly grip the rods. Before it is fastened to the transverse clamps, the transverse rod should be cut to a proper length and bent so that it seats properly in the openings of the transverse clamps on either end.

In FIG. 3 an alternative embodiment of a cross brace assembly is illustrated. Transverse clamps 218 cooperate with transverse rod 30 to form a cross brace assembly for bridging spine rods 14. Each transverse clamp includes lower saddle 220, upper saddle 222, and clamping bolt 24. The differences between the embodiments in FIGS. 2 and 3 will be discussed in more detail below.

Figure 4:
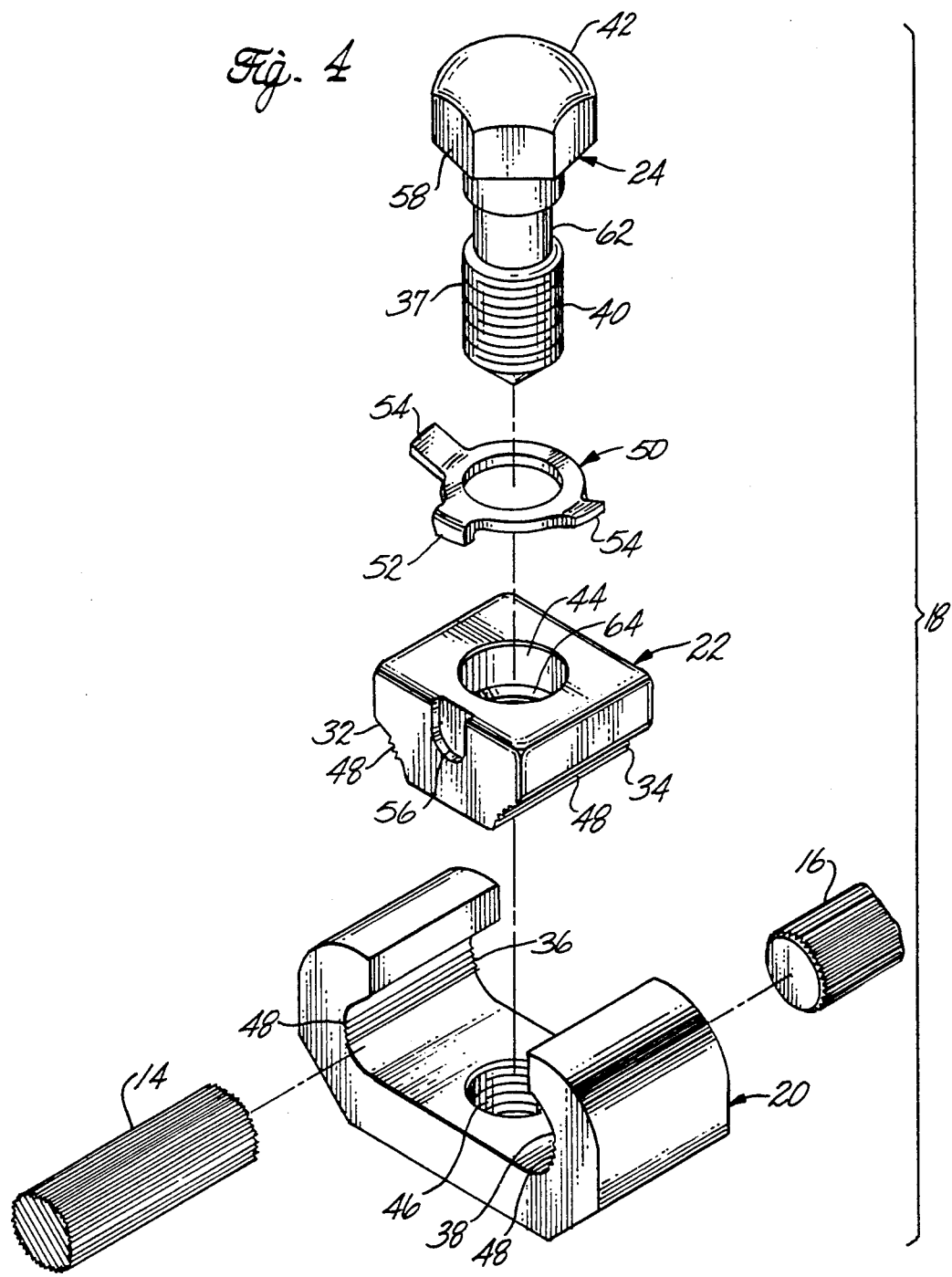
FIG. 4 is an exploded isometric view of a branch connector of the present invention.
Figure 6:
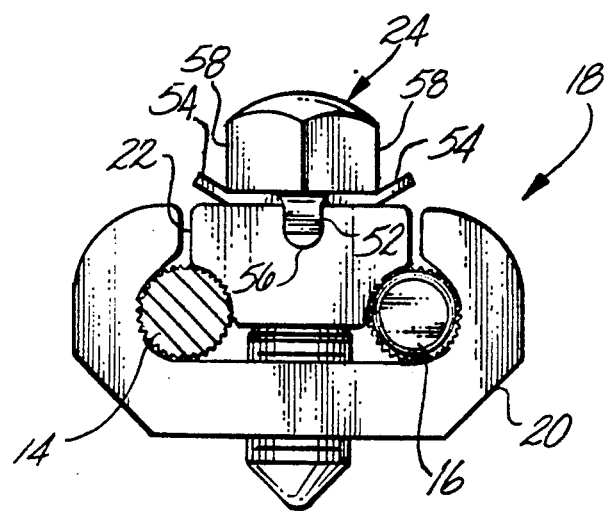
FIG. 6 is an elevation view, partly in section, of a branch connector of the present invention illustrating the lock washer before the bolt has been locked in place.
Figure 7:
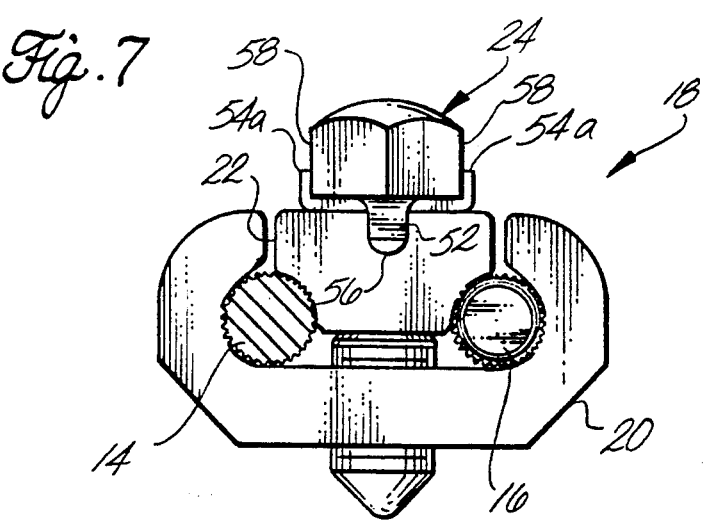
FIG. 7 is an elevation view, partly in section, of a branch connector of the present invention illustrating the lock washer after the bolt has been locked in place.

The details of branch clamp 18 of FIG. 1 are further illustrated in FIG. 4, an exploded isometric view, and FIGS. 6 and 7, elevation views. Lower saddle 20 and upper saddle 22 define arcuate channels 32, 34, 36, and 38 which mate to define a pair of openings for receiving spine rods 14 and 16. Channel 32 on the upper saddle and channel 36 on the lower saddle mate to define the first opening for spine rod 14. Channel 34 on the upper saddle and channel 38 on the lower saddle mate to define the second opening for spine rod 16.

Bolt 24 has a cylindrical shaft 37 which includes a threaded section 40. The shaft extends through a first aperture 44 defined by the upper saddle and threads into a second aperture 46 defined by the lower saddle. The top of hexagonal head 42 of the bolt is preferably rounded in order to reduce irritation of the back muscles once the device is implanted in a patient. Similarly, the corners of the various saddles and other components are generally rounded to avoid irritation.

In the preferred embodiment, spine rods 14 and 16 are longitudinally serrated and the channels of the upper and lower saddles include teeth 48 for gripping the serrations. The teeth run the width of the channel in a direction generally parallel to the direction of the rod that is to be received by the channel. Once assembled, the serrations of the rods and the teeth of the clamp assembly cooperate to provide a firm grip between the rods and transverse clamp, virtually eliminating any later slippage of the device.

Tests have shown that a cross brace assembly using serrated rods and toothed transverse clamps provides exceptional resistance to rotational forces. The addition of a cross brace of this design to a spinal fixation system can as much as quadruple the rotational stiffness of a system without such a cross brace. As proper treatment of a diseased or injured spine requires its complete immobilization, a cross brace of this invention can dramatically improve the effectiveness of a spinal fixation system.

Lock washer 50 interposed between the head of the bolt and the upper saddle is also included in the preferred embodiment. This lock washer locks the bolt in place once the bolt has securely clamped the spine rods within the saddles. An elevation view of a branch clamp including a lock washer is illustrated in FIGS. 6 and 7. The lock washer fits over the shaft of the bolt and includes a lower tab 52 which extends downwardly to cooperate with a notch 56 in the upper saddle to prevent the washer from rotating with respect to the upper saddle. Once the bolt has been tightened to firmly grip the spine rods between the saddles, upper tabs 54 are bent upward against flats 58 on the head of the bolt to prevent the bolt from rotating with respect to the lock washer and upper saddle. It should also be recognized that the flats provide a useful means for gripping the bolt with a tool such as a socket wrench in order to provide the torque necessary to fasten the bolt into the aperture of the lower saddle.

In FIG. 7, the upper tabs 54a are shown after they have been bent to lock against the flats and prevent the bolt from loosening after the device is installed. Initially, before they are locked to the flats, the upper tabs should preferably bend upward slightly. This allows the upper tabs to be grasped and bent more easily, such as with a pair of pliers, once the bolt has been tightened. However, the upward bend must be slight so as to avoid interfering with the flats or any tools used to tighten the bolt.

In the preferred embodiment of a branch connector 18, as it is shown in FIGS. 4, 6 and 7, the lower saddle 20 is C-shaped so that it wraps partially around the upper portions of the two spine rods 14 and 16. The upper saddle 22 is wedge-shaped so that as the saddles are clamped together, the rods are pressed outwardly from the bolt 24 into channels 36 and 38 of the lower saddle. As the bolt is tightened, the downward force of the bolt is redirected outwardly to provide greater leverage for the branch connector in gripping the spine rods.

Referring back to FIG. 4, the preferred embodiment also includes a cylindrical neck 62 around the shaft of the bolt between the head and the threaded section and immediately adjacent the threaded section. This neck cooperates with a threaded lip 64 located inside the aperture of the upper saddle to loosely and rotatably hold the shaft within the upper saddle. The neck and lip allow the bolt, washer and upper saddle to be preassembled so that they can be handled as a single unit during the surgical installation of the device. This preassembly reduces the possibility of misplacing or dropping small parts during the surgical installation of the device.

The bolt, washer and upper saddle are preassembled by first placing the washer in alignment with the first aperture of the upper saddle and pressing the lower tab into the notch. The bolt is then inserted into the first aperture and its threaded section is engaged with the threaded lip. The bolt is threaded past the lip until the threaded section of the bolt is no longer engaged with the lip. The bolt, washer and upper saddle can now be handled as a single unit and the threaded section of the bolt can be inserted and threaded into the second aperture of the lower saddle when ready to connect the pair of rods. Of course, if desired, the unit can be disassembled by the reverse of the assembly procedure.

While the spine rods used in a particular spinal fixation device are generally of the same diameter, this need not always be the case. For example, for a spinal fixation device that extends from the thoracic region of the spine into the cervical region, different diameter spine rods may be desirable. An upper pair of spine rods for the upper cervical region may be of a smaller diameter than a pair of rods in the lower cervical and thoracic region. By configuring a branch connector with different sized channels, a branch connector of this invention can be used to securely connect the different sized rods.

Figure 5:
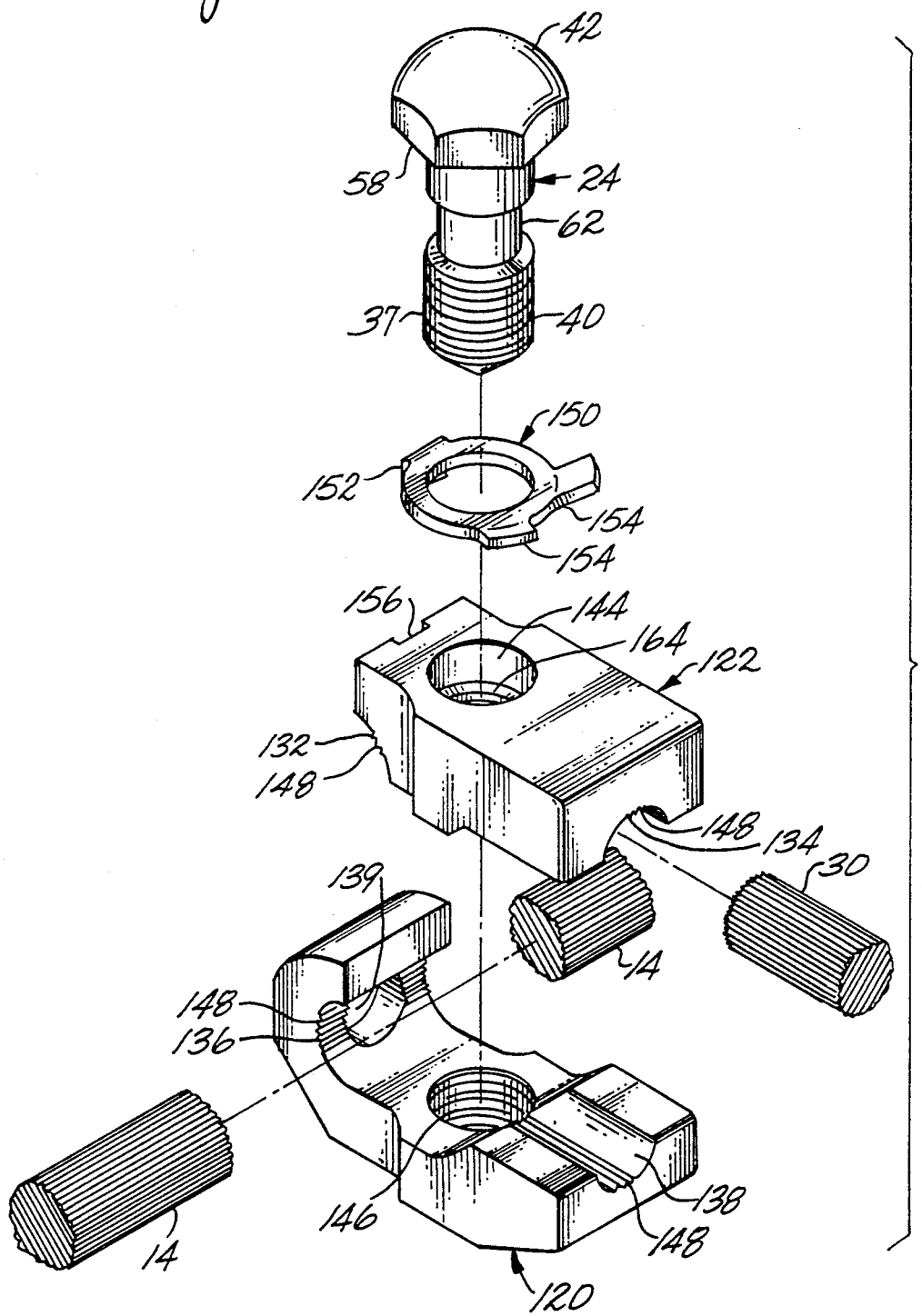
FIG. 5 is an exploded isometric view, partly cut away, of a portion of a transverse cross brace of the present invention.

In the embodiments of FIGS. 2 and 3, the channels are arranged so that branch connectors can be used as transverse clamps in a cross brace assembly. Details of transverse clamp 118 are illustrated in FIG. 5. Upper and lower saddles 122 and 120 cooperate to define openings for receiving spine rod 14 and transverse rod 30. Arcuate channel 132 defined by the upper saddle and arcuate channel 136 defined by the lower saddle mate to define the first opening for receiving spine rod 14. Arcuate channel 134 defined by the upper saddle and arcuate channel 138 defined by the lower saddle mate to define the second opening for receiving an end of transverse rod 30.

In the preferred embodiment of a transverse clamp, the arcuate channel 138 of the lower saddle extends along an imaginary line through an opening 139 in the lower saddle. While this opening has no structural function relating to the use of the transverse clamp, it simplifies fabrication of the lower saddle. The opening provides access to the arcuate channel 138 so that various machines and milling tools can be used to define the shape of the channel and the teeth which later aid in gripping a serrated rod.

Bolt 24 is of the same design as the bolt for the branch connector and includes hexagonal head 42, flats 58, cylindrical shaft 37, threaded section 40, and cylindrical neck 62. The shaft passes through a first aperture 144 in the upper saddle and threads into a second aperture 146 in the lower saddle. The neck cooperates with lip 164 in the first aperture to allow preassembly of the bolt in a way identical to that described above for the branch clamp. Teeth 148 on the channels of the upper and lower saddles improve the grip to the serrated spine rods.

The bolt is located between the first and second openings defined by the channels of the upper and lower saddles. Such placement causes a firm grip of the rods by balancing the forces imparted by the saddles to the rods. Further benefits of such placement include that it allows for compact saddle designs. A compact design generally reduces tissue irritation associated with bulky devices, is generally lighter than a larger device and is simpler to install along a spine rod that also includes several screw-clamp assemblies.

Lock washer 150 has a lower tab 152 which cooperates with notch 156 in the upper saddle to prevent the washer from rotating with respect to the upper saddle. Upper tabs 154 can be bent upward to cooperate with flats 58 on the head of the bolt and prevent the bolt from loosening once the bolt has been properly tightened.

The cross brace is generally assembled after the rest of the spinal fixation system is in place. The lower saddles can be temporarily held in an appropriate place along the spine rods, such as by forceps. A transverse rod is cut to length and bent as necessary so that its ends simultaneously seat in each channel 138 of each lower saddle clamp. The upper saddles can then be bolted and locked into place.

The transverse clamp is preferably configured with a J-shaped lower saddle that forms channel 136 such that the saddle wraps partially around the spine rod. The upper saddle is wedge-shaped at channel 132 on its side toward the spine rod so that as the saddles are clamped together, the spine rod is pressed firmly between the channels with great leverage.

Figure 8:
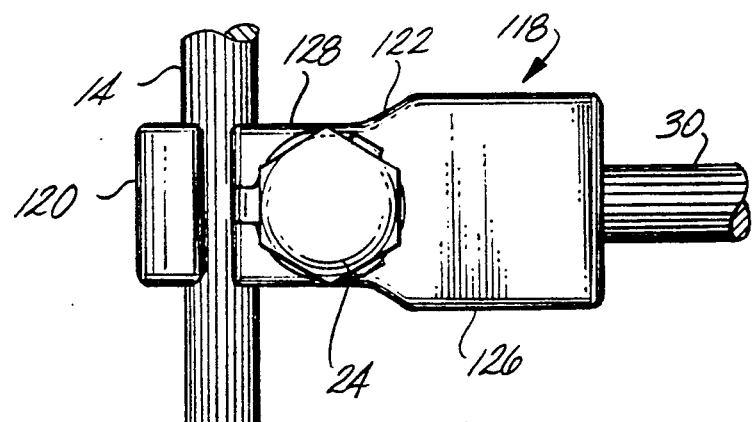
FIG. 8 is a top view of a portion of a transverse cross brace of the present invention.

Another feature of the transverse clamp as shown in FIG. 8 is that the clamp has a tapered end 128 toward the side that grips spine rod 14. A broad end 126 on the opposite end provides firm grip of the transverse rod 30. This tapering is helpful in an installation such as is shown in FIG. 2 where screw clamp assemblies are located at every vertebrae spanned by the spine rod. When the screw clamp assemblies are positioned at every vertebrae, the space along the spine rod between adjacent screw-clamp assemblies can be limited making the attachment of a transverse clamp difficult. By tapering this end of the clamp, the transverse clamp is easy to install in a limited space, yet still provides a strong grip of the transverse rod.

Figure 9:
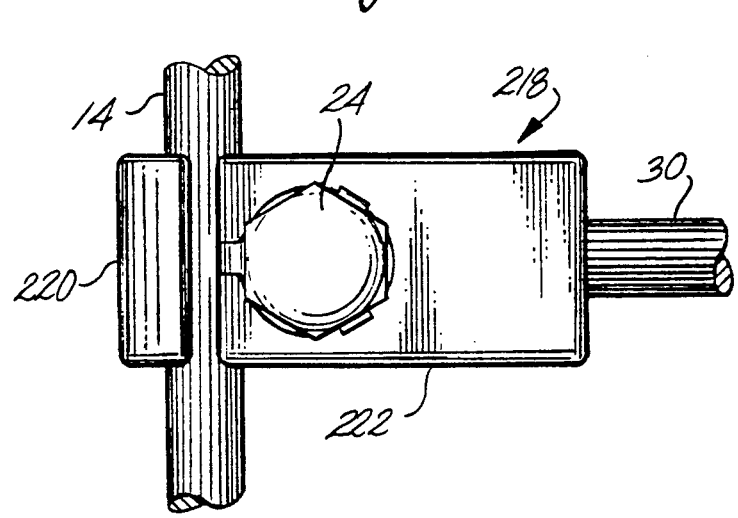
FIG. 9 is a top view of an alternate embodiment of a portion of a transverse cross brace of the present invention.

For installations where a particular vertebrae is skipped as shown in FIG. 3, a non-tapered transverse clamp 218 as shown in FIG. 9, provides slightly better grip of spine rod 14 than a tapered clamp. As with the other branch connectors illustrated, transverse clamp 218 includes a lower saddle 220 and an upper saddle 222 which mate to grip spine rod 14 and transverse rod 30. It should be recognized that neither of the two transverse clamp designs described above are preferred in all applications, but rather, each one has certain advantages over the other in particular circumstances.

The branch connectors of this invention as disclosed thus far, generally have a low profile compared to prior art devices for connecting pairs of spine rods. This is because the devices of this invention keep the two rods to be joined in the same general plane while providing a firm connection between them. However, other embodiments are possible for providing even lower profile connections.

Figure 10:
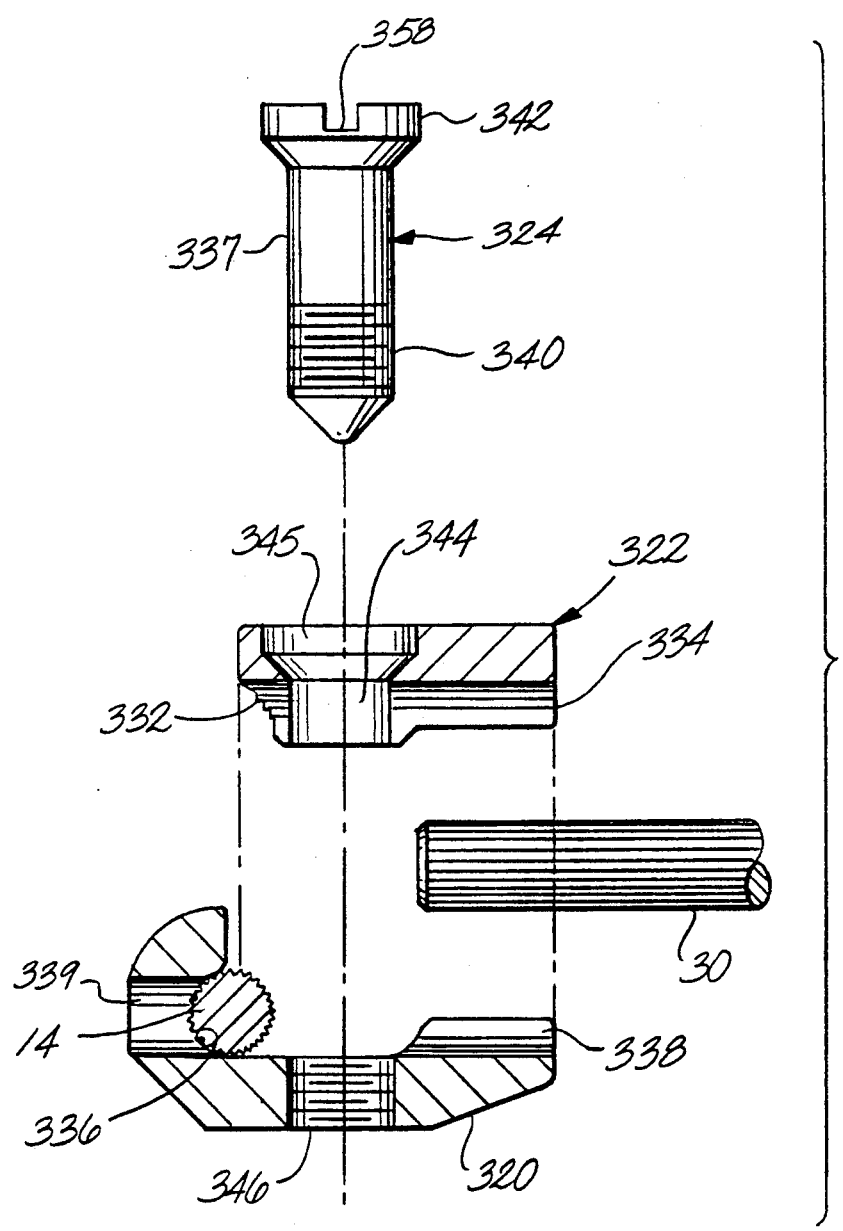
FIG. 10 is an exploded elevation view, partly in section, of another embodiment of a portion of a transverse cross brace of the present invention.
Figure 11:
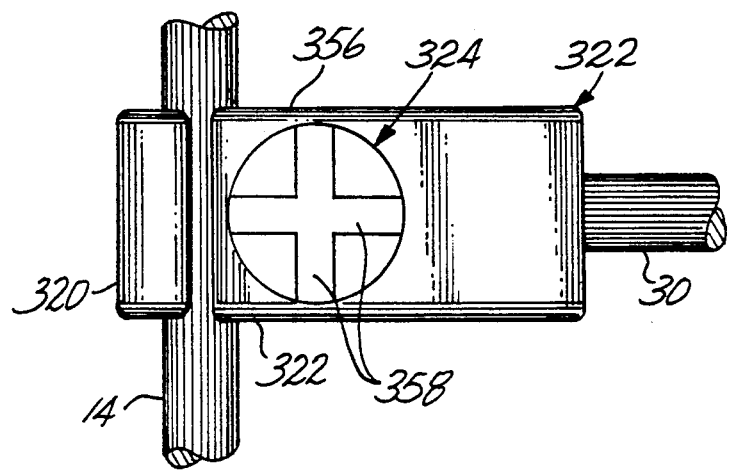
FIG. 11 is a top view of the branch connector of FIG. 10 showing the locking means before the bolt has been locked in place.
Figure 12:
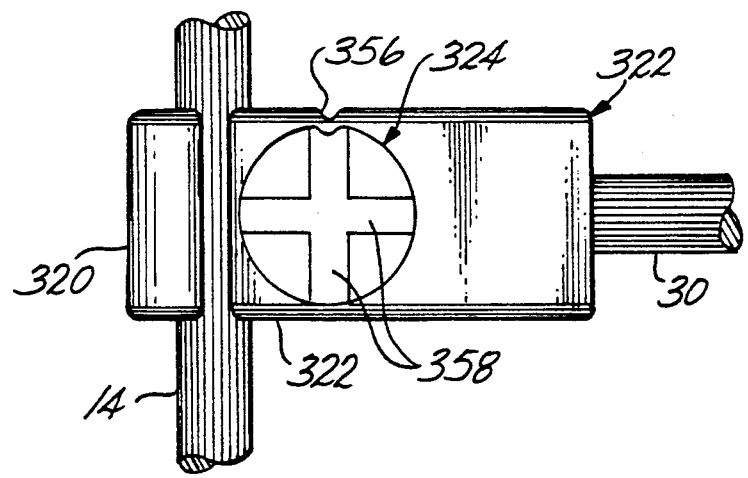
FIG. 12 is a top view of the branch connector of FIG. 10 showing the locking means after the bolt has been locked in place.

In FIGS. 10, 11 and 12 a still lower profile embodiment of a transverse clamp of the present invention is illustrated. This clamp is of the same general design as the other branch connectors. It includes an upper saddle 322 and a lower saddle 320. Spine rod 14 and transverse rod 30 are received in openings defined by arcuate channels. Channels 332 and 336 define an opening for receiving the spine rod and channels 334 and 338 define an opening for receiving one end of the transverse rod. Arcuate channel 338 extends through the lower saddle clamp as aperture 339 to simplify the manufacture of the lower saddle clamp. A bolt 324 which includes a cylindrical head 342, a cylindrical shaft 337 and a threaded section 340 clamps the saddles together to grip the rods. The shaft extends through a first aperture 344 in the upper saddle and threads into a second aperture 346 in the lower saddle.

A particularly low profile design is achieved by seating the head of the bolt within a recess 345 in the upper saddle. The head of the bolt includes perpendicular slots 358 in its upper surface which allow the use of a suitable tool to drive the thread of the bolt into engagement with the threaded second aperture in the lower saddle.

This embodiment further includes means for locking the bolt into place once the rods have been adequately secured within the transverse clamp. A wall 356 of the upper saddle, as illustrated in FIG. 11, is deformed with a suitable tool to create a crimp 356a as illustrated in FIG. 12. The crimp engages with one of slots 358 on the head of the bolt to prevent the bolt from turning and loosening once the clamp has been assembled.

While particular designs for the recess and the head of the bolt are illustrated, numerous other configurations are possible. For example, a sleeve having a stepped configuration that fits into a similarly configured recess in a saddle to clamp a pair of saddles around a spine rod and connect the saddles to a bone screw could be used. While the low profile device of this invention as illustrated is a transverse clamp, it is clear that a similarly designed branch clamp is also possible.

The transverse clamps as illustrated above are generally for use in the lumbar region. However, the devices can easily be scaled down for use in the thoracic or cervical regions of the spine. Similarly, while a transverse rod of the same diameter as the spine rods has been illustrated, the channels of the clamps can be modified to accommodate a transverse rod of a different diameter. The channels can also be modified to accommodate a different shaped rod such as one with an elliptical or polygonal transverse cross section.

The branch connectors of the present invention are preferably made of an alloy capable of resisting corrosion when installed in a human body. It has been found that 316 stainless steel which has been electropolished and passivated to resist corrosion works well. Other metal alloys, such as alloys of titanium also work well.

The present invention is not to be limited to the specific designs shown which are merely illustrative. Various and numerous other arrangements may be devised by one skilled in the art without departing from the spirit and scope of this invention. The scope of the invention is defined in the following claims.

What is claimed is:

1. A connector for connecting a first spine rod to a second rod comprising:
   a wedge-shaped upper saddle and a C-shaped lower saddle, wherein the saddles mate to define a first opening for receiving the first spine rod, and a second opening for receiving the second rod, wherein a longitudinal axis of the first opening and a longitudinal axis of the second opening are in a common plane; and
   means for clamping the saddle together to grip the first and second rods independently of a bone screw wherein the clamping means is located between the first and second openings and wherein the clamping means press the spine rods downwardly and outwardly.

2. The connector recited in claim 1, wherein each of the saddles defines a first channel and a second channel, the first channels for defining the first opening and the second channels for defining the second opening.

3. The connector recited in claim 1, wherein the clamping means comprises a bolt having a head, a shaft and a threaded end, the threaded end extending through a first aperture defined by the upper saddle and threading into a second aperture defined by the lower saddle.

4. The connector recited in claim 3, wherein at least one of the upper and lower saddles includes a plurality of teeth for improving purchase between the saddles and the rods.

5. The connector recited in claim 3, wherein the first and second openings are arranged generally parallel to one another for receiving generally parallel rods.

6. The connector recited in claim 3 further comprising means for locking the bolt in place.

7. The connector recited in claim 6, wherein the locking means comprises a lock washer between the head of the bolt and the upper saddle, the lock washer having a plurality of tabs, at least one tab for gripping the upper saddle and at least one tab being deformable for gripping the head of the bolt.

8. The connector recited in claim 3, wherein the upper saddle defines a recess for receiving the head of the bolt.

9. The connector recited in claim 8 further comprising means for locking the bolt in place.

10. The connector recited in claim 9, wherein the locking means comprises a deformable wall defined by the upper saddle adjacent to and for deformable engagement with the head of the bolt for preventing rotation of the bolt.

11. The connector recited in claim 3, wherein the first aperture of the upper saddle is at least partially threaded to cooperate with the threaded end of the bolt, and the bolt further comprises a neck around the shaft and between the head and the threaded end, wherein the bolt can be preassembled to the upper saddle by threading the threaded end of the bolt through the at least partially threaded first aperture.

12. A cross brace assembly for connecting generally parallel and spaced apart first and second spine rods to one another, the assembly comprising:
   a transverse rod having first and second ends; and
   first and second connectors, each connector comprising an upper saddle, a lower saddle and means for clamping the saddles together wherein the saddles of the first connector mate to define a first opening for receiving the first spine rod and a second opening for receiving the first end of the transverse rod wherein the first and second openings are in a common plane, the clamping means for the first connector being located between the first and second openings, and the saddles of the second connector mate to define a third opening for receiving the second spine rod, and a fourth opening for receiving the second end of the transverse rod wherein the third and fourth openings are in a common plane, the clamping means for the second connector being located between the third and fourth openings.

13. The cross brace assembly recited in claim 12, wherein each of the saddles defines a first channel and a second channel, wherein for the first connector, the first channels define the first opening and the second channels define the second opening, and for the second connector, the first channels define the third opening and the second channels define the fourth opening.

14. The cross brace assembly recited in claim 12, wherein the clamping means for each connector comprises a bolt having a head, a shaft and a threaded end, the threaded end for extending through a first aperture defined by the upper saddle and threading into a second aperture defined by the lower saddle.

15. The cross brace assembly recited in claim 14, wherein at least one of the upper and lower saddles includes a plurality of teeth for improving purchase between the saddles and the rods.

16. The cross brace assembly recited in claim 14, wherein each connector further comprises means for locking the bolt in place.

17. The cross brace assembly recited in claim 16, wherein, for each connector, the locking means comprises a lock washer between the head of the bolt and the upper saddle, the lock washer having a plurality of tabs, at least one tab for gripping the upper saddle and at least one tab being deformable for gripping the head of the bolt.

18. The cross brace assembly recited in claim 14, wherein each upper saddle includes a recess for receiving the head of the bolt.

19. The cross brace assembly recited in claim 18 further comprising means for locking each bolt in place.

20. The cross brace assembly recited in claim 19, wherein, for each connector, the locking means comprises a deformable wall defined by each upper saddle adjacent to and for deformable engagement with the head of the bolt.

21. The cross brace assembly recited in claim 14, wherein the first aperture of each upper saddle is at least partially threaded to cooperate with the threaded end of each bolt, and each bolt further comprises a neck around the shaft and between the head and the threaded end, wherein each bolt can be preassembled to each upper saddle by threading the threaded end of each bolt through the first aperture of each upper saddle.

22. A connector for connecting a first spine rod to a second spine rod comprising:
a J-shaped lower saddle which includes two channels adapted to receive the first and second spine rods, one in each of the channels, wherein one of the channels wraps partially around one of the rods;
an upper saddle which includes two channels, one of which is wedge-shaped, to matingly engage the two channels of the lower saddle to thereby grip the rods in a first and second opening formed by the matingly engaged channels; and
means for clamping the upper saddle to the lower saddle independently of a bone screw wherein the clamping means is located between the first and second openings and comprises a bolt having a head, a shaft and a threaded end, the threaded end extending through a first aperture defined by the upper saddle and threading into a second aperture defined by the lower saddle wherein the first aperture of the upper saddle is at least partially threaded to cooperate with the threaded end of the bolt, and the bolt further comprises a neck around the shaft and between the head and the threaded end, wherein the bolt can be preassembled to the upper saddle by threading the upper end of the bolt through that at least partially threaded first aperture.

23. The connector recited in claim 22, wherein a longitudinal axis of the first opening and a longitudinal axis of the second opening are in a common plane.

24. The connector recited in claim 22, wherein at least one of the upper and lower saddles includes a plurality of teeth for improving purchase between the saddles and the rods.

25. The connector recited in claim 22, further comprising a lock washer between the head of the bolt and the upper saddle, the lock washer having a plurality of tabs, at least one tap for gripping the upper saddle and at least one tab being deformable for gripping the head of the bolt to thereby lock the bolt in place.

26. The connector recited in claim 22, wherein the upper saddle defines a recess for receiving the head of the bolt.

27. The connector recited in claim 22 further comprising a deformable wall defined by the upper saddle adjacent to and for deformable engagement with the head of the bolt for preventing rotation of the bolt to thereby lock the bolt in place.

28. A connector for connecting a first spine rod to a second spine rod comprising:
an upper saddle adapted for gripping the two spine rods and having a first aperture which is at least partially threaded;
a lower saddle adapted to mate with the upper saddle in gripping the two spine rods and having a threaded second aperture wherein the lower saddle is C-shaped and the upper saddle is wedge-shaped so that the bolt clamping means presses the spine rods downwardly and outwardly; and
a bolt comprising a head, a shaft and a threaded end for placing through the first and second apertures to thereby clamp the upper saddle to the lower saddle for gripping the two spine rods, wherein the bolt can be preassembled to the upper saddle by threading the upper end of the bolt through that at least partially threaded first aperture.

* * * * *

UNITED STATES PATENT AND TRADEMARK OFFICE
CERTIFICATE OF CORRECTION

PATENT NO. : 5,330,473
DATED : July 19, 1994
INVENTOR(S) : Robert S. Howland

It is certified that error appears in the above-indentified patent and that said Letters Patent is hereby corrected as shown below:

Column 3, line 2, change "than" to -- that --.

Column 4, line 51, before "spine" insert -- a --.

Column 5, line 5, change "center line" to
      -- centerline --.

Column 6, line 6, after "serrations" insert a period.

Column 9, line 65, change "saddle" to -- saddles --.

Column 12, line 25, change "tap" to -- tab --.

Signed and Sealed this

Seventh Day of February, 1995

Attest:

BRUCE LEHMAN

*Attesting Officer*  *Commissioner of Patents and Trademarks*